United States Patent [19]

Dellaria et al.

[11] Patent Number: 5,407,959

[45] Date of Patent: Apr. 18, 1995

[54] TRANS-1,4-DIALKOXYCYCLOHEXYL) SUBSTITUTED ARYLALKYLARYL-ARYLALKENYLARYL-, AND ARYLALKYNYLARYLUREA INHIBITORS OF 5-LIPOXYGENASE

[75] Inventors: Joseph F. Dellaria, Lindenhurst; Anwer Basha, Lake Forest; Lawrence A. Black, Vernon Hills; Linda J. Chernesky, Arlington Heights; Wendy Lee, Chicago, all of Ill.

[73] Assignee: Abbott Laboratories, Abbott Park, Ill.

[21] Appl. No.: 152,115

[22] Filed: Nov. 12, 1993

[51] Int. Cl.$^6$ .................. A61K 31/17; C07C 275/06; C07C 275/30
[52] U.S. Cl. .................. 514/598; 514/227.5; 514/237.8; 514/239.5; 514/255; 514/329; 514/478; 514/567; 514/596; 544/59; 544/164; 544/382; 546/224; 560/27; 562/452; 564/47; 564/48; 564/52; 564/53; 564/54
[58] Field of Search ................ 564/52, 53, 54, 47, 564/48; 514/596, 598

[56] References Cited

U.S. PATENT DOCUMENTS

| 4,289,903 | 9/1981 | Spatz et al. | 564/52 |
| 5,015,762 | 5/1991 | Schirmer et al. | 564/52 |

FOREIGN PATENT DOCUMENTS

| 0041145 | 12/1981 | European Pat. Off. | 514/596 |
| 0375404 | 6/1990 | European Pat. Off. | C07D 309/10 |
| 0375457 | 8/1990 | European Pat. Off. | C07D 317/22 |
| 0385662 | 9/1990 | European Pat. Off. | C07D 405/12 |
| 0385663 | 9/1990 | European Pat. Off. | C07D 215/22 |
| 0409412 | 1/1991 | European Pat. Off. | C07D 317/18 |
| 0462812 | 12/1991 | European Pat. Off. | C07D 409/04 |

OTHER PUBLICATIONS

C. Crawley, et al., *J. Med. Chem.*, 1992, 35, 2600–2609.

*Primary Examiner*—Shailendra Kumar
*Attorney, Agent, or Firm*—Jerry F. Janssen

[57] ABSTRACT

Compounds of structure

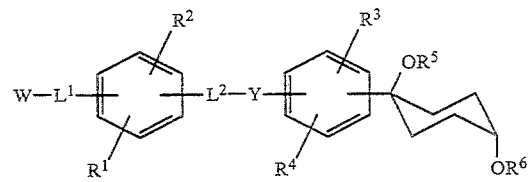

where W is selected from the group consisting of

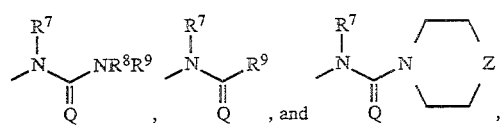

where Q is oxygen or sulfur, $R^7$ and $R^8$ are independently selected from hydrogen and alkyl, or $R^7$ and $R^8$, together with the nitrogen atoms to which they are attached, define a radical of formula

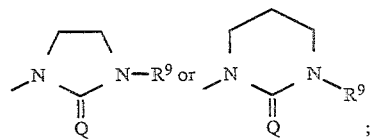

$L^1$ and $L^2$ are independently selected from a valence bond, alkylene, propenylene, and propynylene; $R^1$, $R^2$, $R^3$, and $R^4$ are independently selected from alkyl, alkoxy, haloalkyl, halogen, cyano, amino, alkoxycarbonyl, and dialkylaminocarbonyl; Y is oxygen, $>NR^{11}$, where $R^{11}$ is hydrogen or alkyl, or $$-\overset{(O)_n}{S}-,$$

where n=0, 1, or 2; and $R^5$ and $R^6$ are alkyl, inhibit the biosynthesis of leukotrienes. These compounds are useful in the treatment or amelioration of allergic and inflammatory disease states.

7 Claims, No Drawings

TRANS-1,4-DIALKOXYCYCLOHEXYL) SUBSTITUTED ARYLALKYLARYL-ARYLALKENYLARYL-, AND ARYLALKYNYLARYLUREA INHIBITORS OF 5-LIPOXYGENASE

TECHNICAL FIELD

This invention relates to compounds having biological activity to inhibit lipoxygenase enzymes, to pharmaceutical compositions comprising these compounds, and to a medical method of treatment. More particularly, this invention concerns certain triether-containing compounds which inhibit leukotriene biosynthesis, to pharmaceutical compositions comprising these compounds and to a method of inhibiting lipoxygenase activity and leukotriene biosynthesis.

BACKGROUND OF THE INVENTION

5-Lipoxygenase is the first dedicated enzyme in the pathway leading to the biosynthesis of leukotrienes. This important enzyme has a rather restricted distribution, being found predominantly in leukocytes and mast cells of most mammals. Normally 5-lipoxygenase is present in the cell in an inactive form; however, when leukocytes respond to external stimuli, intracellular 5-lipoxygenase can be rapidly activated. This enzyme catalyzes the addition of molecular oxygen to fatty acids with cis,cis-1,4-pentadiene structures, converting them to 1-hydroperoxy-trans,cis-2,4-pentadienes. Arachidonic acid, the 5-lipoxygenase substrate which leads to leukotriene products, is found in very low concentrations in mammalian cells and must first be hydrolyzed from membrane phospholipids through the actions of phospholipases in response to extracellular stimuli. The initial product of 5-lipoxygenase action on arachidonate is 5-HPETE which can be reduced to 5-HETE or converted to LTA$_4$. This reactive leukotriene intermediate is enzymatically hydrated to LTB$_4$ or conjugated to the tripeptide glutathione to produce LTC$_4$. LTA$_4$ can also be hydrolyzed nonenzymatically to form two isomers of LTB$_4$. Successive proteolytic cleavage steps convert LTC$_4$ to LTD$_4$ and LTE$_4$. Other products resulting from further oxygenation steps have also been described in the literature. Products of the 5-lipoxygenase cascade are extremely potent substances which produce a wide variety of biological effects, often in the nanomolar to picomolar concentration range.

The remarkable potencies and diversity of actions of products of the 5-lipoxygenase pathway have led to the suggestion that they play important roles in a variety of as diseases. Alterations in leukotriene metabolism have been demonstrated in a number of disease states including asthma, allergic rhinitis, rheumatoid arthritis and gout, psoriasis, adult respiratory distress syndrome, inflammatory bowel disease, endotoxin shock syndrome, atherosclerosis, ischemia induced myocardial injury, and central nervous system pathology resulting from the formation of leukotrienes following stroke or subarachnoid hemorrhage.

The enzyme 5-lipoxygenase catalyzes the fast step leading to the biosynthesis of all the leukotrienes and therefore inhibition of this enzyme provides an approach to limit the effects of all the products of this pathway. Compounds which inhibit 5-lipoxygenase are thus useful in the treatment of disease states such as those listed above in which the leukotrienes play an important role.

SUMMARY OF THE INVENTION

In its principal embodiment, the present invention provides certain triether compounds which inhibit lipoxygenase enzyme activity and are useful in the treatment of allergic and inflammatory disease states in which leukotrienes play a role.

The compounds of this invention and the pharmaceutically acceptable salts thereof have the structure

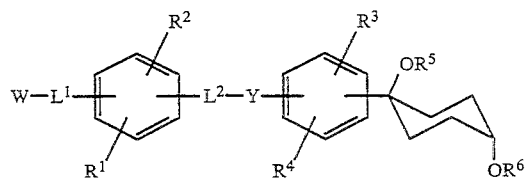

wherein W is selected from the group consisting of

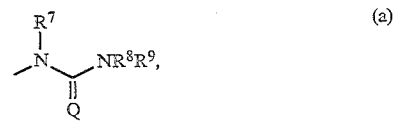  (a)

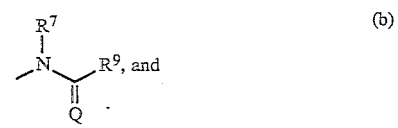  (b)

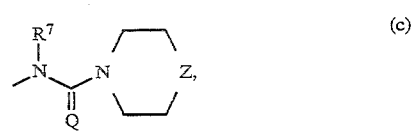  (c)

where Q is oxygen or sulfur, $R^7$ and $R^8$ are independently selected from hydrogen and alkyl of one to four carbon atoms, or $R^7$ and $R^8$, together with the nitrogen atoms to which they are attached, define a radical of formula

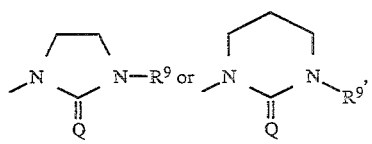

provided that when $L^1$ is a valence bond, $R^7$ is alkyl of one to four carbon atoms.

$R^9$ is selected from (a) hydrogen, (b) alkyl of one to four carbon atoms, (c) haloalkyl of one to four carbon atoms, (d) cyanoalkyl of one to four carbon atoms, (e) phenyl, optionally substituted with alkyl of one to four carbon atoms, alkoxy of one to four carbon atoms, haloalkyl, or halogen, cyano, carboxyl, carboxyalkyl or two to six carbon atoms, and dialkylaminocarbonyl in which the two alkyl groups are independently of one to four carbon atoms, (f) hydroxyalkyl of one to four carbon atoms, (g) aminoalkyl of one to four carbon atoms, (h) carboxyalkyl of one to four carbon atoms, (i) (alkoxycarbonyl)alkyl where the alkyl and alkoxy portions each are of one to four carbon atoms, and (j) (alkylaminocarbonyl)alkyl, where the alkyl and aminoalkyl portions each are of one to four carbon atoms, and Z is —CH$_2$—, oxygen, sulfur, or —NR$^{10}$ where R$^{10}$ is hydrogen or alkyl of one to four carbon atoms.

L$^1$ and L$^2$ are independently selected from the group consisting of a valence bond, alkylene of one to three carbon atoms, propenylene, and propynylene. R$^1$, R$^2$, R$^3$, and R$^4$ are independently selected from alkyl of one to four carbon atoms, alkoxy of one to four carbon atoms, haloalkyl, halogen, cyano, amino, carboxyl, alkoxycarbonyl of one to four carbon atoms, alkylamino of one to four carbon atoms, dialkylamino where the two alkyl groups are independently of one to four carbon atoms, and dialkylaminocarbonyl where the alkyl portions are each of one to four carbon atoms. Y is oxygen, >NR$^{11}$, where R$^{11}$ is hydrogen or alkyl of one to four carbon atoms, or

where n=0, 1, or 2, and R$^5$ and R$^6$ are independently selected from hydrogen, alkyl of one to four carbon atoms, alkenyl of two to four carbon atoms, and alkynyl or two to four carbon atoms.

DETAILED DESCRIPTION OF THE INVENTION

Definitions of Terms

As used throughout this specification and the appended claims, the term "alkyl" refers to a monovalent group derived from a straight or branched chain saturated hydrocarbon by the removal of a single hydrogen atom. Alkyl groups are exemplified by methyl, ethyl, n- and iso-propyl, n-, sec-, iso- and tert-butyl, and the like.

The term "alkylamino" refers to a group having the stucture —NHR' wherein R' is alkyl as previously defined. Example of alkylamino include methylamino, ethylamino, iso-propylamino, and the like.

The term "alkylaminocarbonyl" refers to an alkylamino group, as previously defined, attached to the parent molecular moiety through a carbonyl group. Examples of alkylaminocarbonyl include methylaminocarbonyl, ethylaminocarbonyl, isopropylaminocarbonyl, and the like.

The term "alkanoyl" refers to an alkyl group, as defined above, attached to the parent molecular moiety through a carbonyl group. Alkanoyl groups are exemplified by formyl, acetyl, butanoyl, and the like.

The term "propynyl" refers to a straight chain, three-carbon group containing a carbon-carbon triple bond.

The term "hydroxyalkyl" represents an alkyl group, as defined above, substituted by one to three hydroxyl groups with the proviso that no more than one hydroxy group may be attached to a single carbon atom of the alkyl group.

The term "haloalkyl" denotes an alkyl group, as defined above, having one, two, or three halogen atoms attached thereto and is exemplified by such groups as chloromethyl, bromoethyl, trifluoromethyl, and the like.

The terms "alkoxy" and "alkoxyl" denote an alkyl group, as defined above, attached to the parent molecular moiety through an oxygen atom. Representative alkoxy groups include methoxyl, ethoxyl, propoxyl, butoxyl, and the like.

The term "alkoxycarbonyl" represents an ester group; i.e. an alkoxy group attached to the parent molecular moiety through a carbonyl group. Representative alkoxycarbonyl groups include methoxycarbonyl, ethoxycarbonyl, and the like.

The term "alkenyl" denotes a monovalent group derived from a hydrocarbon containing at least one carbon-carbon double bond by the removal of a single hydrogen atom. Alkenyl groups include, for example, ethenyl, propenyl, butenyl, 1-methyl-2-buten-1-yl and the like.

The term "alkylene" denotes a divalent group derived from a straight or branched chain saturated hydrocarbon by the removal of two hydrogen atoms, for example methylene, 1,2-ethylene, 1,1-ethylene, 1,3-propylene, 2,2-dimethylpropylene, and the like.

The term "aminoalkyl" denotes an —NH$_2$ group attached to the parent molecular moiety through an alkylene group. Representative aminoalkyl groups include 2-amino-1-ethylene, 3-amino-1-propylene, 2-amino-1-propylene, and the like.

The term "carboxyalkyl" denotes a —CO$_2$H group attached to the parent molecular moiety through an alkylene group. Representative carboxyalkyl groups include, 1-carboxyethyl, 2-carboxyethyl, 1-carboxypropyl, and the like.

The term "(alkoxycarbonyl)alkyl" denotes an alkoxycarbonyl group, as defined above, attached to the parent molecular moiety through an alkylene group. Representative (alkoxycarbonyl)alkyl groups include ethoxycarbonylmethyl, ethoxycarbonylethyl, methoxycarbonylpropyl, and the like.

The term "(alkylaminocarbonyl)alkyl" denotes an alkylaminocarbonyl group, as defined above, attached to the parent molecular moiety through an alkylene group. Examples of (alkylaminocarbonyl)alkyl groups include methylaminocarbonylmethyl, methylaminocarbonylpropyl, isopropylaminocarbonylmethyl, and the like.

The term "alkenylene" denotes a divalent group derived from a straight or branched chain hydrocarbon containing at least one carbon-carbon double bond. Examples of alkenylene include —CH=CH—, —CH$_2$CH=CH—, —C(CH$_3$)=CH—, —CH$_2$CH=CHCH$_2$—, and the like.

In one preferred embodiment, the compounds of this invention have the structure

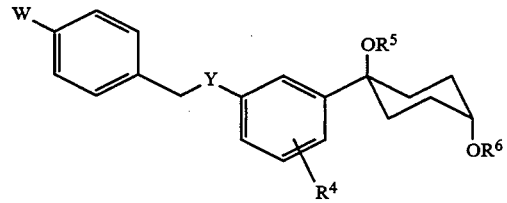

wherein W, Y, R$^4$, R$^5$, and R$^6$ are as defined above.

Examples of compounds of this embodiment include, but are not limited to:

trans-1,4-dimethoxy-4-[3-(4-(N-acetyl-N-methylamino)-benzyloxy)-5-fluorophenyl]cyclohexane, trans-1,4-dimethoxy-4-[3-(4-(N-acetyl-N-methylamino)-benzyloxy)phenyl]cyclohexane, trans-1,4-dimethoxy-4-[3-(4-(N',N'-dimethylaminocarbonyl-N-methylamino)benzyloxy)-5-fluorophenyl]-cyclohexane, trans-1,4-dimethoxy-4-[3-(4-(N',N'-dimethylaminocarbonyl-N-methylamino)benzyloxy)phenyl]cyclohexane,
trans-1,4-dimethoxy-4-[3-(4-(N', N'-dimethylaminothiocarbonyl-N-methylamino) benzyloxy)-5-fluorophenyl]cyclohexane,
trans-1,4-dimethoxy-4-[3-(4-(N',N'-dimethylaminocarbonyl-N-methylamino)benzylthio)-5-fluorophenyl]cyclohexane,
trans-1,4-dimethoxy-4-[3-(4-(N-acetyl-N-methylamino)-benzylthio)-5-fluorophenyl]cyclohexane,
trans-1,4-dimethoxy-4-[3-(4-(N',N'-dimethylaminocarbonyl-N-methylamino)benzylamino)phenyl]cyclohexane,
trans-1,4-dimethoxy-4-[3-(4-(N-acetyl-N-methylamino)-benzylamino)-5-fluorophenyl]cyclohexane,
trans-1,4-dimethoxy-4-[3-(4-(N-aminocarbonyl-N-methylamino)benzyloxy)-5-fluorophenyl]cyclohexane,
trans-1,4-dimethoxy-4-[3-(4-(N'-methylamino-N-methylamino)benzyloxy)-5-fluorophenyl]cyclohexane,
trans-1,4-dimethoxy-4-[3-(4-(N-(1-piperidinylcarbonyl)-N-methylamino)benzyloxy)-5-fluorophenyl]cyclohexane,
trans-1,4-dimethoxy-4-[3-(4-(N-(4-morpholinocarbonyl)-N-methylamino)benzyloxy)-5-fluorophenyl]cyclohexane,
trans-1,4-dimethoxy-4-[3-(4-(N-(4-thiomorpholinocarbonyl)-N-methylamino)benzyloxy-5-fluorophenyl]cyclohexane,
trans-1,4-dimethoxy-4-[3-(4-(N-(1-piperazinylcarbonyl)-N-methylamino)benzyloxy)-5-fluorophenyl]cyclohexane,
trans-1,4-dimethoxy-4-[3-(4-((N'-(3-bromoprop-1-yl)aminocarbonyl)-N-methylamino) benzyloxy)-5-fluorophenyl]cyclohexane,
trans-1,4-dimethoxy-4-[3-(4-((N'-(3-aminoprop-1-yl)aminocarbonyl)-N-methylamino) benzyloxy)-5-fluorophenyl]cyclohexane,
trans-1,4-dimethoxy-4-[3-(4-((N'-(3-hydroxyprop-1-yl)aminocarbonyl)-N-methylamino)benzyloxy)-5-fluorophenyl]cyclohexane,
trans-1,4-dimethoxy-4-[3-(4-((3-ethoxycarbonylprop-1-yl)aminocarbonyl)-N-methylamino)benzyloxy)-5-fluorophenyl]cyclohexane,
trans-1,4-dimethoxy-4-[3-(4-((3-carboxyprop-1-yl)aminocarbonyl)-N-methylamino)benzyloxy)-5-fluorophenyl]cyclohexane,
trans-1,4-dimethoxy-4-[3-(4-((N'-(3-bromoprop-1-yl)-N'-methylaminocarbonyl)-N-methylamino) benzyloxy)-5-fluorophenyl]cyclohexane,
trans-1,4-dimethoxy-4-[3-(4-((N'-(3-aminoprop-1-yl)-N'-methylaminocarbonyl)-N-methylamino) benzyloxy)-5-fluorophenyl]cyclohexane,
trans-1,4-dimethoxy-4-[3-(4-((3-ethoxycarbonylprop-1-yl)-N'-methylaminocarbonyl)-N-methylamino) benzyloxy)-5-fluorophenyl]cyclohexane,
trans-1,4-dimethoxy-4-[3-(4-((3-carboxyprop-1-yl)-N'-methylaminocarbonyl)-N-methylamino) benzyloxy)-5- fluorophenyl]cyclohexane,
trans-1,4-dimethoxy-4-[3-(4-((N'-(3-aminoprop-1-yl)-N'methylaminocarbonyl)-N-methylamino) benzyloxy)-5-fluorophenyl]cyclohexane,
trans-1,4-dimethoxy-4-[3-(4-((N'-(3-hydroxyprop-1-yl)-N'-methylaminocarbonyl)-N-methylamino) benzyloxy)-5-fluorophenyl]cyclohexane,
trans-1,4-dimethoxy-4-[3-(4-((3-ethoxycarbonylprop-1-yl)-N'-methylaminocarbonyl)-N-methylamino) benzyloxy)-5-fluorophenyl]cyclohexane,
trans-1,4-dimethoxy-4-[3-(4-((3-carboxyprop-1-yl)-N'-methylaminocarbonyl)-N-methylamino) benzyloxy)-5-fluorophenyl]cyclohexane,
trans-1,4-dimethoxy-4-[3-(4-((3-N''-methylaminocarbonylprop-1-yl)aminocarbonyl)-N-methylamino)-benzyloxy)-5-fluorophenyl]cyclohexane,
trans-1,4-dimethoxy-4-[3-(4-(N-(3-bromoprop-1-ylcarbonyl)-N-methylamino) benzyloxy)-5-fluorophenyl]cyclohexane,
trans-1,4-dimethoxy-4-[3-(4-(N-(3-aminoprop-1-ylcarbonyl)-N-methylamino) benzyloxy)-5-fluorophenyl]cyclohexane,
trans-1,4-dimethoxy-4-[3-(4-(N-(3-hydroxyprop-1-ylcarbonyl)-N-methylamino) benzyloxy)-5-fluorophenyl]cyclohexane,
trans-1,4-dimethoxy-4-[3-(4-(N-(3-ethoxycarbonylprop-1-ylcarbonyl)-N-methylamino) benzyloxy)-5-fluorophenyl]cyclohexane,
trans-1,4-dimethoxy-4-[3-(4-(N-(3-carboxyprop-1-ylcarbonyl)-N-methylamino) benzyloxy)-5-fluorophenyl]cyclohexane, and
trans-1,4-dimethoxy-4-[3-(4-(N-(3-N'-methylaminocarbonylprop-1-ylcarbonyl)-N-methylamino) benzyloxy)-5-fluorophenyl]cyclohexane.

In another preferred embodiment, the compounds of this invention have the structure

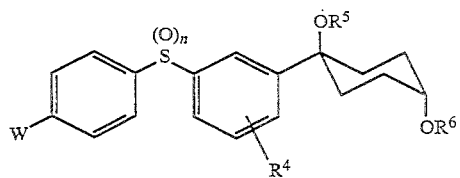

wherein W, $R^4$, $R^5$, $R^6$, and n are as defined above.
Examples of compounds of this embodiment include, but are not limited to
trans-1,4-dimethoxy-4-[3-(4-(N',N'-dimethylaminocarbonyl-N-methylamino)phenylthio)phenyl]cyclohexane,
trans-1,4-dimethoxy-4-[3-(4-(N',N'-dimethylaminocarbonyl-N-methylamino)phenylsulfinyl)phenyl]cyclohexane,
trans-1,4-dimethoxy-4-[3-(4-(N',N'-dimethylaminocarbonyl-N-methylamino)phenylsulfonyl)phenyl]cyclohexane,
trans-1,4-dimethoxy-4-[3-(4-(N-acetyl-N-methylamino)phenylthio)phenyl]cyclohexane,
trans-1,4-dimethoxy-4-[3-(4-(N-acetyl-N-methylamino)phenylsulfinyl)phenyl]cyclohexane, and
trans-1,4-dimethoxy-4-[3-(4-(N-acetyl-N-methylamino)phenylsulfonyl)phenyl]cyclohexane.
Particularly preferred compounds of this invention are trans-1,4-dimethoxy-4-[3-(4-(N-acetyl-N-methylamino)benzyloxy)-5-fluorophenyl]cyclohexane, trans-1,4-dimethoxy-4-[3-(4-(N',N'-dimethylaminocarbonyl-N-methylamino)benzyloxy)-5-fluorophenyl]cyclohexane, trans-1,4-dimethoxy-4-[3-(4-(N',N'-dimethylaminocarbonyl-N-methylamino)phenylthio)phenyl]cyclohexane, trans-1,4-dimethoxy-4-[3(4-(N- acetyl-N-methylamino)phenylthio)phenyl]cyclohexane, and the pharmaceutically acceptable salts thereof.

Lipoxygenase Inhibition Determination

Inhibition of leukotriene biosynthesis was evaluated in an assay, involving calcium ionophore-induced $LTB_4$ biosynthesis expressed human whole blood. Human heparinized whole blood was preincubated with test compounds or vehicle for 15 min at 37° C. followed by calcium ionophore A23187 challenge (final concentration of 8.3 μM) and the reaction terminated after 30 min by adding two volumes of methanol containing prostaglandin $B_2$ as an internal recovery standard. The methanol extract was analyzed for $LTB_4$ using a commercially available radioimmunoassay.

Using this test, representative compounds of this invention were found to inhibit leukotriene biosynthesis.

Pharmaceutical Compositions

The present invention also provides pharmaceutical compositions which comprise compounds of the present invention formulated together with one or more non-toxic pharmaceutically acceptable carriers. The pharmaceutical compositions may be specially formulated for oral administration in solid or liquid form, for parenteral injection, or for rectal administration.

The pharmaceutical compositions of this invention can be administered to humans and other animals orally, rectally, parenterally, intracisternally, intravaginally, intraperitoneally, topically (as by powders, ointments, or drops), bucally, or as an oral or nasal spray. The term "parenteral" administration as used herein refers to modes of administration which include intravenous, intramuscular, intraperitoneal, intrasternal, subcutaneous and intraarticular injection and infusion.

Pharmaceutical compositions of this invention for parenteral injection comprise pharmaceutically acceptable sterile aqueous or nonaqueous solutions, dispersions, suspensions or emulsions as well as sterile powders for reconstitution into sterile injectable solutions or dispersions just prior to use. Examples of suitable aqueous and nonaqueous careers, diluents, solvents or vehicles include water, ethanol, polyols (such as glycerol, propylene glycol, polyethylene glycol, and the like), and suitable mixtures thereof, vegetable oils (such as olive oil), and injectable organic esters such as ethyl oleate. Proper fluidity can be maintained, for example, by the use of coating materials such as lecithin, by the maintenance of the required particle size in the case of dispersions, and by the use of surfactants.

These compositions may also contain adjuvants such as preservatives, wetting as agents, emulsifying agents, and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents such as sugars, sodium chloride, and the like. Prolonged absorption of the injectable pharmaceutical form may be brought about by the inclusion of agents which delay absorption such as aluminum monostearate and gelatin.

In some cases, in order to prolong the effect of the drug, it is desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly(orthoesters) and poly(anhydrides) Depot injectable formulations are also prepared by entrapping the drug in liposomes or microemulsions which are compatible with body tissues.

The injectable formulations can be sterilized, for example, by filtration through a bacterial-retaining filter, or by incorporating sterilizing agents in the form of sterile solid compositions which can be dissolved or dispersed in sterile water or other sterile injectable medium just prior to use.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or mill sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

The active compounds can also be in micro-encapsulated form, if appropriate, with one or more of the above-mentioned excipients.

Liquid dosage forms for oral administration include pharmaceutically acceptable emulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, and perfuming agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar, and tragacanth, and mixtures thereof.

Compositions for rectal or vaginal administration are preferably suppositories which can be prepared by mixing the compounds of this invention with suitable nonirritating excipients or carriers such as cocoa butter, polyethylene glycol or a suppository wax which are solid at room temperature but liquid at body temperature and therefore melt in the rectum or vaginal cavity and release the active compound.

Compounds of the present invention can also be administered in the form of liposomes. As is known in the art, liposomes are generally derived from phospholipids or other lipid substances. Liposomes are formed by mono- or multilamellar hydrated liquid crystals that are dispersed in an aqueous medium. Any non-toxic, physiologically acceptable and metabolizable lipid capable of forming liposomes can be used. The present compositions in liposome form can contain, in addition to a compound of the present invention, stabilizers, preservatives, excipients, and the like. The preferred lipids are the phospholipids and the phosphatidyl cholines (lecithins), both natural and synthetic.

Methods to form liposomes are known in the art. See, for example, Prescott, Ed., *Methods in Cell Biology*, Volume XIV, Academic Press, New York, N.Y. (1976), p. 33 et seq.

Dosage forms for topical administration of a compound of this invention include powders, sprays, ointments and inhalants. The active compound is mixed under sterile conditions with a pharmaceutically acceptable carrier and any needed preservatives, buffers, or propellants which may be required. Opthalmic formulations, eye ointments, powders and solutions are also contemplated as being within the scope of this invention.

Actual dosage levels of active ingredients in the pharmaceutical compositions of this invention may be varied so as to obtain an amount of the active compound(s) that is effective to achieve the desired therapeutic response for a particular patient, compositions, and mode of administration. The selected dosage level will depend upon the activity of the particular compound, the route of administration, the severity of the condition being treated, and the condition and prior medical history of the patient being treated. However, it is within the skill of the art to start doses of the compound at levels lower than required for to achieve the desired therapeutic effect and to gradually increase the dosage until the desired effect is achieved.

Generally dosage levels of about 1 to about 50, more preferably of about 5 to about 20 mg of active compound per kilogram of body weight per day are administered orally to a mammalian patient. If desired, the effective daily dose may be divided into multiple doses for purposes of administration, e.g. two to four separate doses per day.

Preparation of the Compounds of the Invention

The compounds of this invention can be prepared by a variety of synthetic routes. Representative procedures are outlined as follows. It should be understood that $L^1$, $R^5$, $R^6$, $R^7$, $R^8$, $R^9$, $R^{10}$, and W, as used herein, correspond to the groups identified above.

In general, the compound of this invention are prepared by alkylation of 1 as shown in Scheme 1.

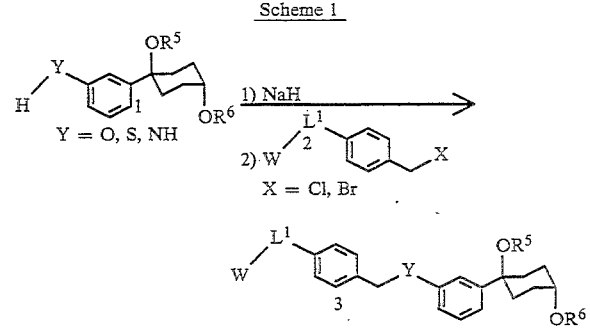

The preparation of 1 is shown in Scheme 2. 3-bromophenol is converted to O-naphthylmethyl intermediate 4 by standard methodology. Treatment of 4 with n-butyl lithium and quenching of the resulting aryl anion with the mono-ethylene ketal of cyclohexane-1,4-dione provides alcohol 5 which is alkylated by treatment with sodium hydride and alkyl halide. Subsequent deprotection with aqueous hydrochloric acid in acetone provides ketone 7. Selective reduction of the ketone with LS-Selectride (lithium tris-i-amylborohydride) provides axial alcohol 8, to the near exclusion of the equatorial isomer. Alkylation of 8 as described above provides trans diether 9. The napthyl group is removed by hydrogenolysis (10% Pd/C, H2, ethanol) to give 1.

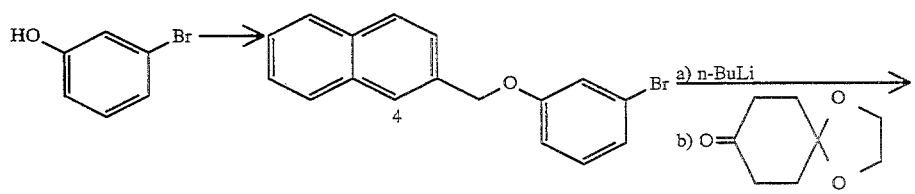

-continued
Scheme 2

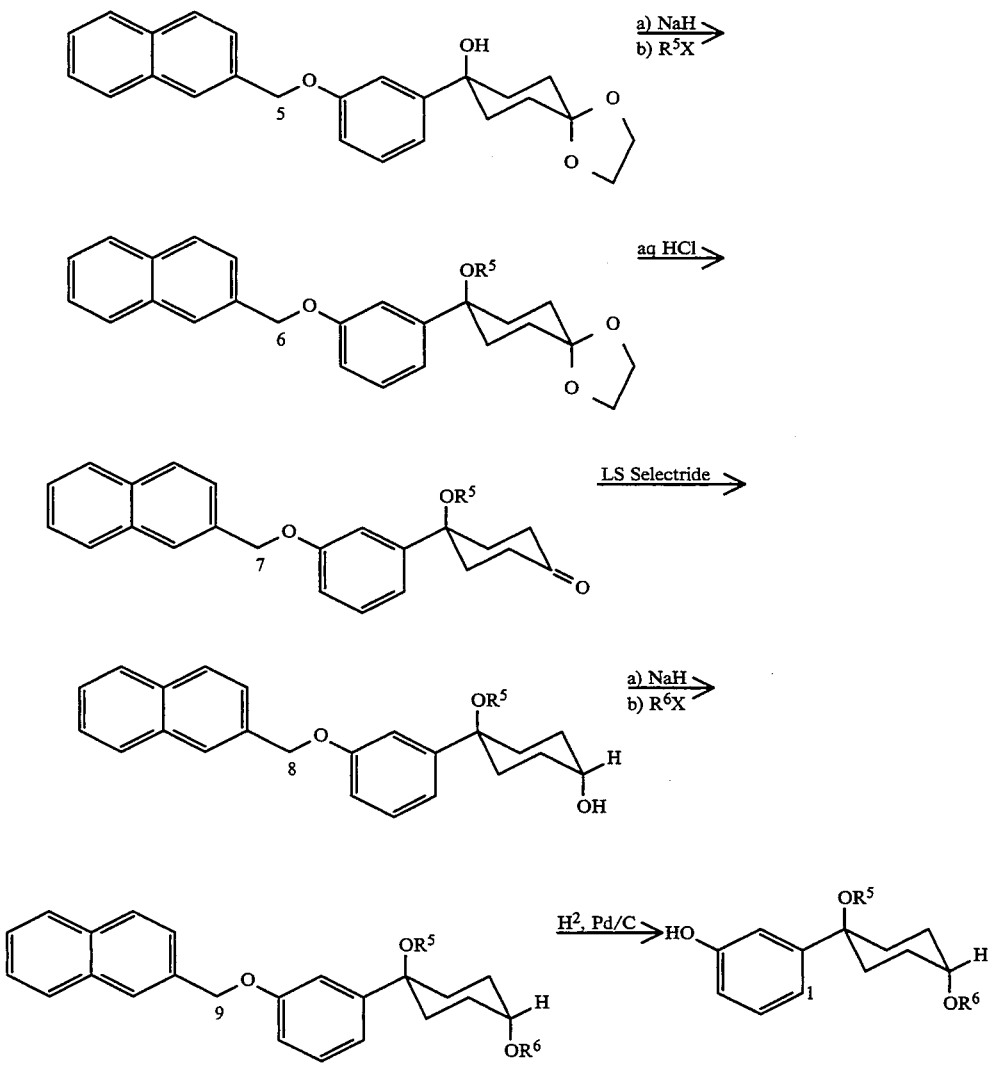

The preparation of compounds where $R^7$ is alkyl is shown in Reaction Scheme 3. The methyl ester of 4-aminobenzoic acid is treated allyloxycarbonyl chloride to produce 10. Reaction of 10 with sodium hydride and the desired alkyl halide, $R^7X$ yields 11 in which the nitrogen is substituted by the alkyl group derived from the alkyl halide. Treatment of 11 with the lithio salt of triethylborane ("superhydride"), followed by reaction with sodium hydride and 4-methoxy-4-(3-iodo-propenyl)-tetrahydropyran yields 12. Reaction of 12 with either palladium or rhodium removes the group from the nitrogen of the phenyl ring to yield 13 which can be reacted with trimethylsilylisocyanate to yield the N-$R^7$-substituted urea, 14, or with alkyl lithium, followed by $R^8R^9NC(O)Cl$ to produce the N-$R^7$,N',N'-$R^9$,$R^9$-substituted urea, 15.

Scheme 3

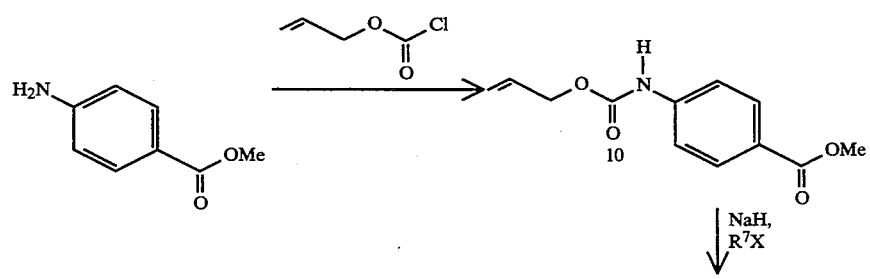

Scheme 3

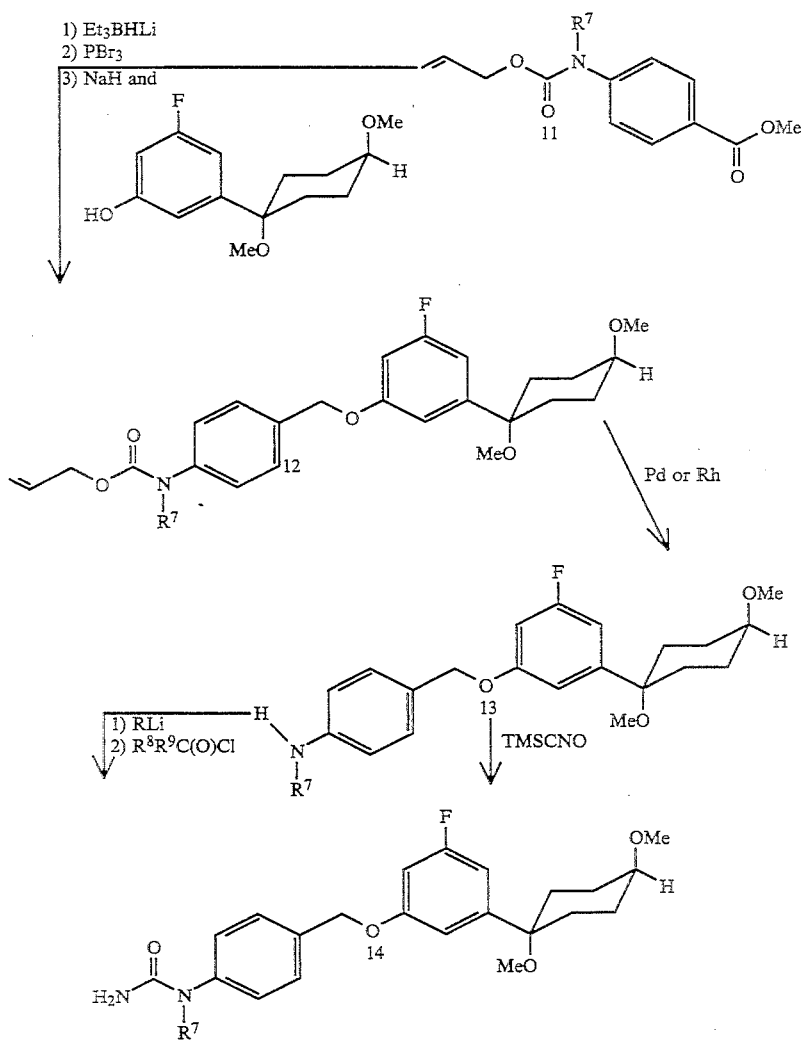

The preparation of the compounds of this invention where $R^9$ is haloalkyl, or aminoalkyl is shown in Scheme 4. Amine 16, prepared as in scheme 3, is treated with the desired haloalkylisocyanate to form haloalkyl derivative 19. Conversion of 19 to azide 20, followed by reduction of the azide with 1,3-propanedithiol provides aminoalkyl derivative 21. Compounds in which $R^8$ is alkyl are prepared by alkylation of 20 followed by reduction with propanedithiol as described above.

Scheme 4

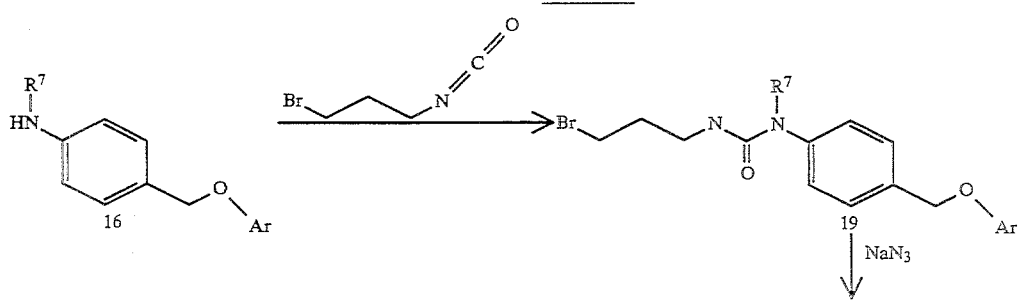

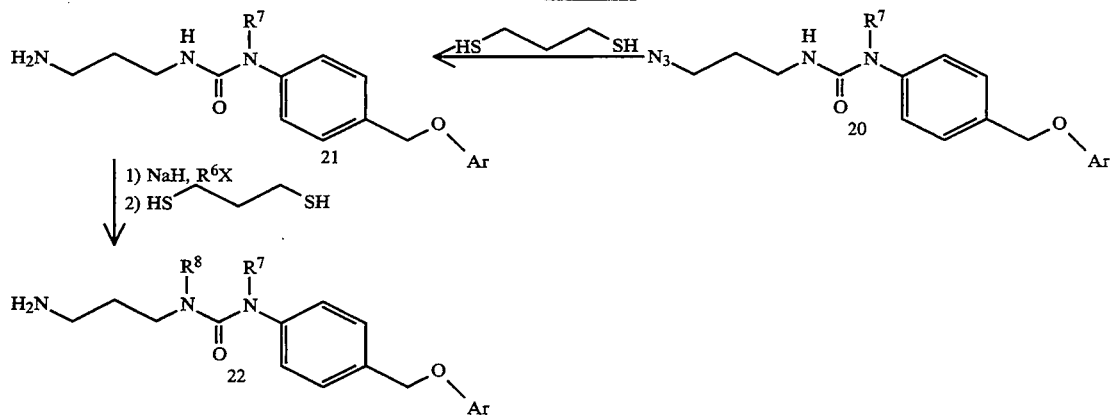

The preparation of the compounds of this invention where R[9] is hydroxyalkyl, carboxyalkyl, (alkoxycarbonyl)alkyl, or (alkylaminocarbonyl)alkyl, is shown in Scheme 5. Amine 16 is treated with an alkoxycarbonylalkylisocyanate to provide the alkoxycarbonylalkyl derivative 23, which is alkylated by treatment with NaH and R[8]X. Hydrolysis of ester 24 provides (alkoxycarbonyl)alkyl derivative 25. Reduction of 24 with lithium borohydride or 25 with BH$_3$ provides the hydroxyalkyl compound 26. Ester 23 is hydrolyzed or reduced as described above to prepare the derivatives wherein R[8] is H. The (alkylaminocarbonyl)alkyl derivatives are prepared from esters 23 and 24, or acids 25 and 27 by standard synthetic methods.

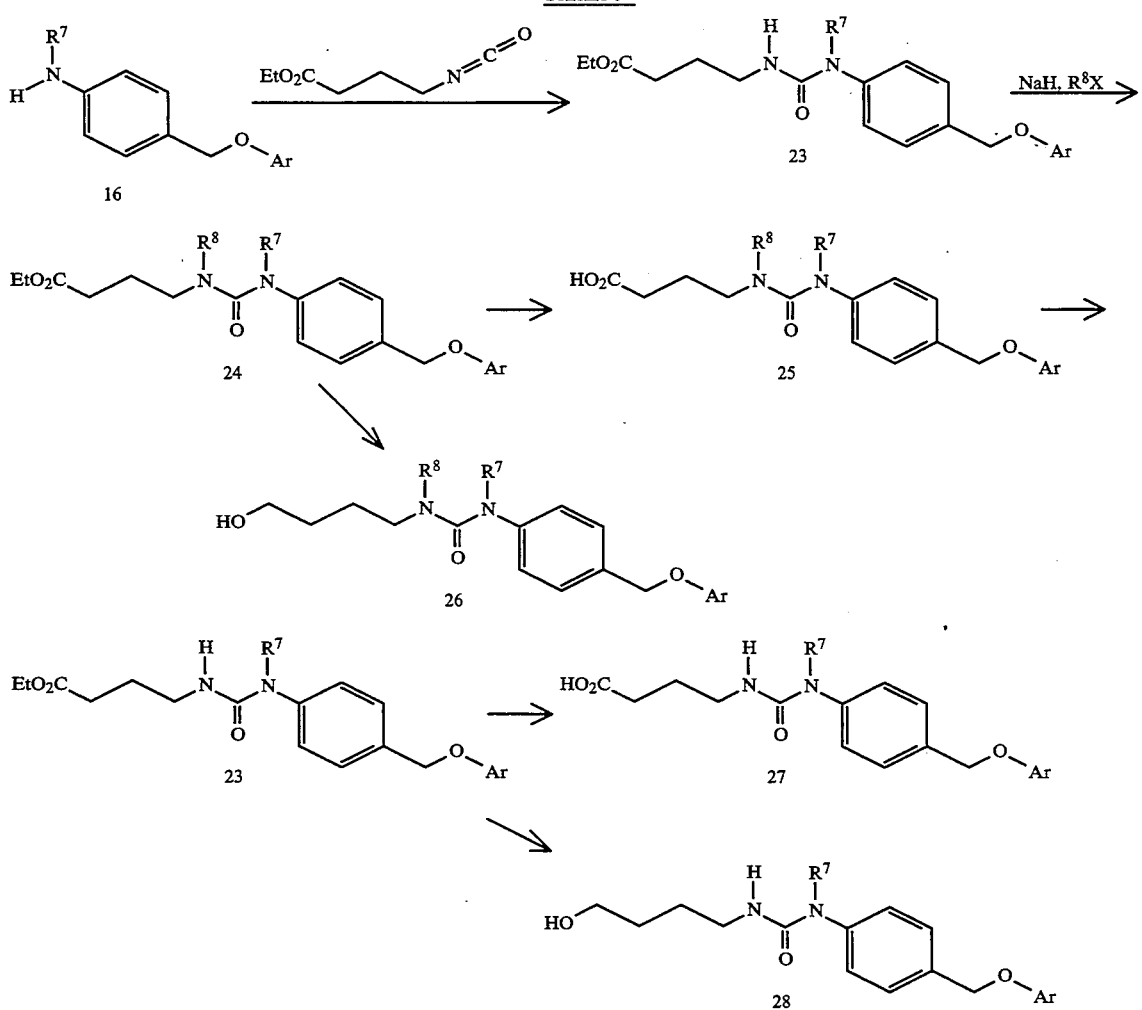

The preparation of N-acyl compounds is shown in Scheme 6. Methyl 4-(N-methylamino)benzoate is acylated with allyl chloroformate for form 29. Benzyl chloride 30 is prepared by reduction of the ester with lithium triethylborohydride and treatment of the resulting benzyl alcohol with PCl$_3$. Arylalkyl-aryl ether 31 is then prepared from chloride 30 as described in Scheme 1. Carbamate 31 is hydrolyzed according to the method of Corey, E. J., and Suggs, J. W., *J. Org. Chem.*, 1973, 38, 3223, and the resulting amine is acylated by treatment with lithium hexamethyldisylazide and 4-pentenoyl chloride to form 32. Reaction of 32 with borane-pyridine forms alcohol 33, which is oxidized to 34 by treatment with Jone's reagent. Amide 35 is prepared by the DCC-catalyzed coupling of 34 and R$^8$R$^9$NH.

Alcohol 33 is converted to primary iodide 36 by treatment with methanesulfonyl chloride and NaI. Displacement of iodide with NaCN produces alkylcyano derivative 37. Displacement of iodide with NaN$_3$, followed by reduction of the azide with 1,3-propanedithiol forms alkylamine 38.

The preparation of the arylpropynyl-, arylpropenyl-, and arylpropyl-aryl ethers is shown in Scheme 7. 4-iodoaniline is converted to urea 39 by acylation with dimethylcarbamyl chloride, followed by alkylation with NaH and MeI. Coupling of 39 with propargyl alcohol as described in EPA 385 663, provides propynol 40. Mitsunobu coupling (triphenylphosphine, diethyzaxodicarboxylate) of 40 with 1 affords the desired compound 42.

Treatment of alkynol 40 with Red-Al (sodium bis(2-methoxyethoxy)aluminum hydride) and coupling of the resulting allylic alcohol with 1 as described above provides 44. Catalytic hydrogenation of 44 provides saturated compound 45.

Scheme 7

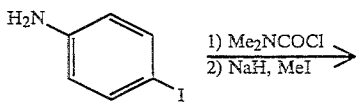

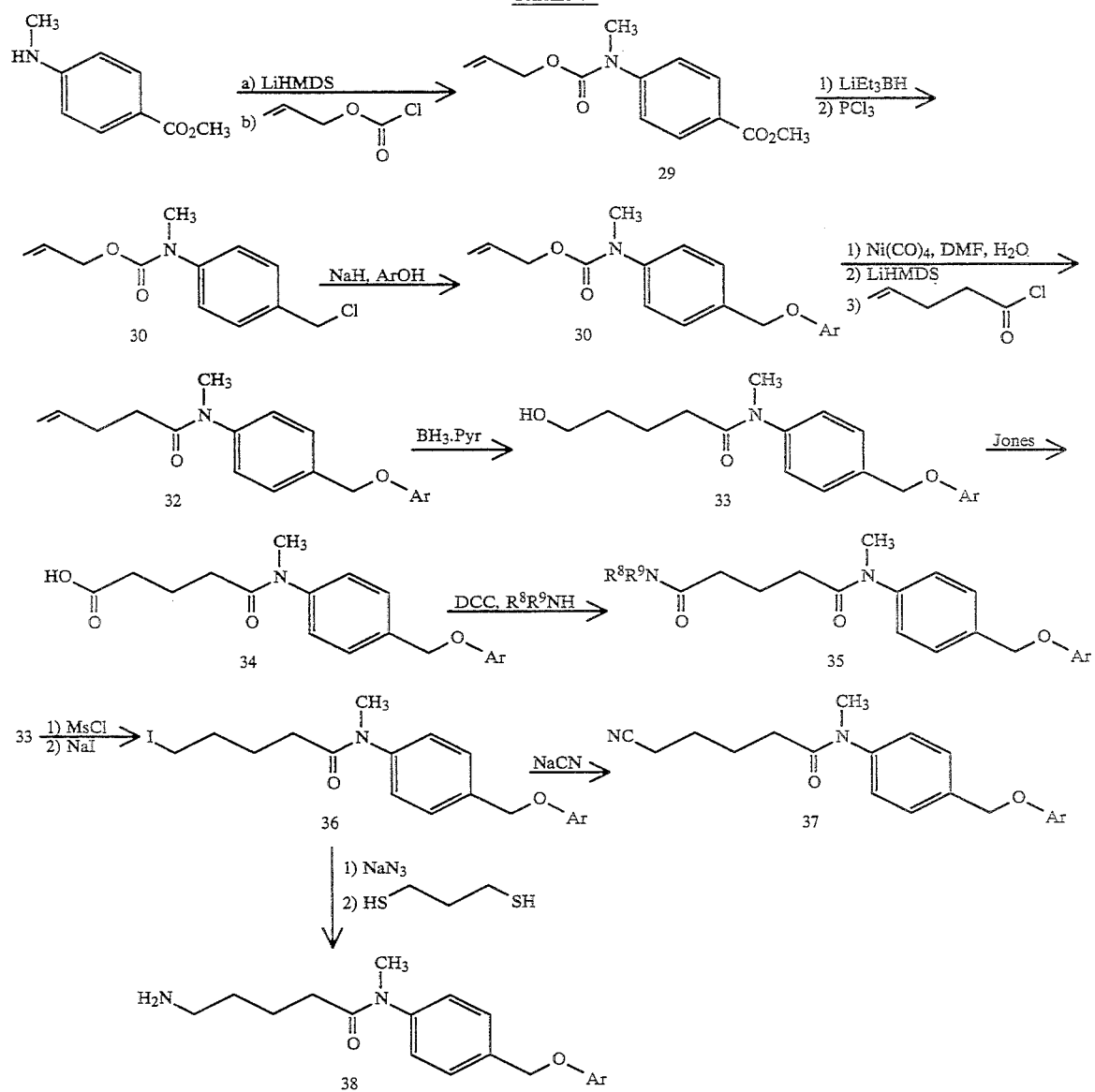

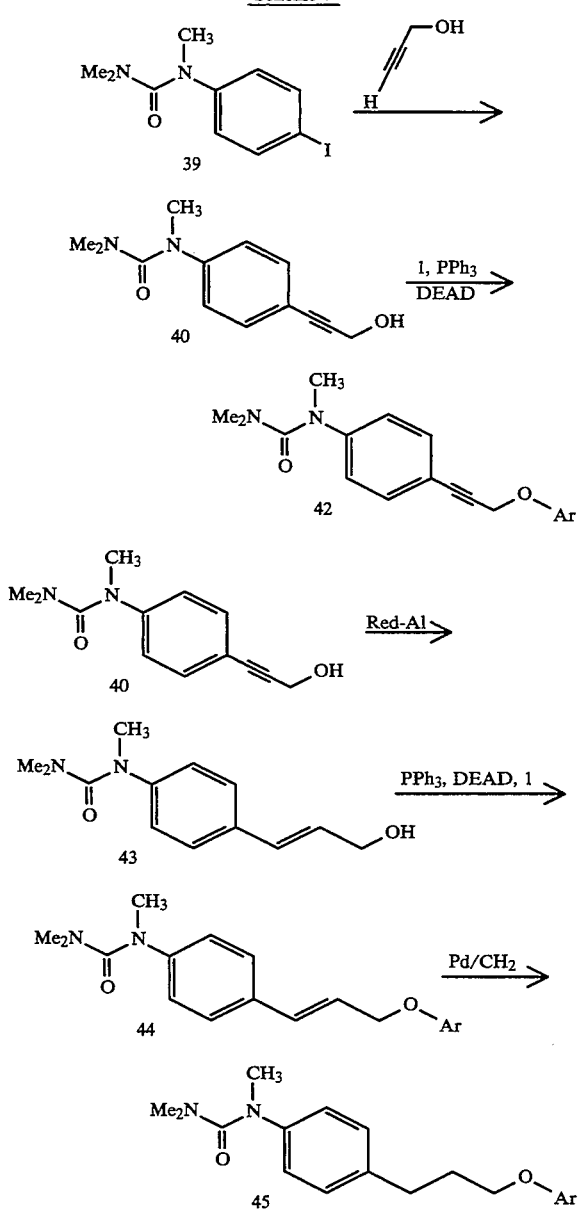

The foregoing may be better understood by the following examples which are presented for the purpose of illustration and not intended to limit the scope of the inventive concept.

EXAMPLE 1

Preparation of trans-1,4-dimethoxy-4-[3-(4-(N-acetyl-N-methylamino)-benzyloxy)-5-fluorophenyl]cyclohexane Step 1. 4-hydroxy-4-[3-(naphth-2-ylmethyloxy)-5-fluorophenyl]cyclohexan-1-one ethylene glycol ketal The desired compound was prepared by treatment of 3-(napth-2-ylmethyloxy)-5-fluorobromobenzene, prepared as described in EPA 385 679, with n-butyllithium and 1,4-cycloheaxanedione mono-ethylene glycol ketal.

Step 2. 4-methoxy-4-[3-(naphth-2-ylmethyloxy)-5-fluorophenyl]cyclohexan-1-one ethylene glycol ketal The desired compound was prepared by reaction of 4-hydroxy-4-[3-(naphth-2-ylmethyloxy)-5-fluorophenyl]cyclohexan-1-one ethylene glycol ketal, prepared as in step 1, with NaH and iodomethane.

Step 3. 4-methoxy-4-[3-(napth-2-ylmethyloxy)-5-fluorophenyl]cyclohexan-1-one

The desired compound was prepared by hydrolysis of 4-methoxy-4-[3-(naphth-2-ylmethyloxy)-5-fluorophenyl]cyclohexan-1-one ethylene glycol ketal, prepared as in step 2, with aqueous HCl in ethanol.

Step 4. Trans-4-methoxy-4-[3-(napth-2-ylmethyloxy)-5-fluorophenyl]cyclohexan-1-ol The desired compound was prepared by reduction of a solution in THF of 4-methoxy-4-(3-[napth-2-ylmethyloxy)-5-fluorophenyl]cyclohexan-1-one, prepared as in step 3, with LS-selctride at $-78°$ C.

Step 5. Trans-1,4-dimethoxy-4-[3-(napth-2-ylmethyloxy)-5-fluorophenyl]cyclohexane The desired compound was prepared as in step 2, except substituting trans-4-methoxy-4-[3-(napth-2-ylmethyloxy)-5-fluorophenyl]cyclohexan-1-ol, prepared as in step 4, for 4-hydroxy-4-[3-(naphth-2-ylmethyloxy)-5-fluorophenyl]cyclohexan-1-one ethylene glycol ketal.

Step 6. Trans- 1,4-dimethoxy-4-(3-hydroxy-5-fluorophenyl)cyclohexane

Exposure of trans-1,4-dimethoxy-4-[3-(napth-2-ylmethyloxy)-5fluorophenyl]cyclohexane, prepared as in step 5, to 10% Pd/C and 4 atmospheres of hydrogen in methanol at ambient temperature for 17 hours provided trans-1,4-dimethoxy-4-(3-hydroxy-5-fluorophenyl)cyclohexane.

Step 7. 4-(N-acetyl-N-methylamino)benzoic acid

To a solution of N-methyl-4-aminobenzoic acid (2.0 g, 13.2 mmol) in anhydrous pyridine (13.2 mL) was added acetic anhydride (1.4 mL, 14.5 mmol). The reaction was stirred at ambient temperature until TLC indicated complete reaction (~22 hours). The resultant solution was poured into ethyl acetate and the organic phase was washed (3×10% HCl; 1×water; 1×brine), dried (MgSO4), filtered and concentrated in vacuo to provide the amide as a colorless solid. Recrystallization (ethyl acetate/hexane) afforded 4-(N-acetyl-N-methylamino)benzoic acid (2.15 g, 84.0%). $^1$H NMR (300 MHz, CDCl$_3$) δ 8.18 (2H, br d, J=8.5 Hz), 7.33 (2H, br d, J=8.5 Hz), 3.33 (3H, s), 2.0 (3H, br s). MS m/e 194 (M+H)$^+$, 211 (M+NH$_4$)$^+$.

Step 8. 4-(N-acetyl-N-methylamino)benzyl alcohol

An oven dried flask, under nitrogen flow, was charged with a stir bar, 4-(N-acetyl-N-methylamino)benzoic acid (1.0 g, 5.18 mmol), prepared as in step 7, anhydrous DME (10.3 mL), and anhydrous DMF (3.0 mL). The resulting solution was cooled to $-20°$ C., and 4-methylmorpholine (0.60 mL, 5.4 mmol) and isobutyl chloroformate (0.70 mL, 5.4 mmol) were added sequentially via syringe. The reaction mixture was stirred under N$_2$ at $-20°$ C. for 1 hour. The resultant yellow mixture was filtered and the precipitate washed with DME (2×~1 mL). The combined flitrate and washings were cooled to 0° C. and sodium borohydride (800 mg, 21.1 mmol) dissolved in water (2.0 mL) was added dropwise. The reaction was stirred at 0° C. for 15 min. and quenched with saturated aqueous ammonium chloride. The resulting mixture was partitioned between ethyl acetate and brine. The combined organic layers were dried (MgSO4), filtered and concentrated in vacuo to give an oil. Purification by flash chromatography on silica gel (90% ethyl acetate/hexane) provided 4-(N-acetyl-N-methylamino)benzyl alcohol as a colorless oil which solidified on standing. Recrystallization from hexane provided the alcohol as a colorless solid (543.0 mg, 58.5%). mp 83.5°–85.5° C. $^1$H NMR (300 MHz, CDCl$_3$) δ 7.45 (2H, d, J=8.5 Hz), 7.18 (2H, d, J=8.5 Hz), 4.75 (2H, s), 3.27 (3H, s), 1.90 (3H, MS m/e 180 (M+H)$^+$, 197 (M+NH$_4$)$^+$.

Step 9. 4-(N-acetyl-N-methylamino)benzyl bromide

To a solution of 4-(N-acetyl-N-methylamino)benzyl alcohol (543.0 mg, 3.0 mmol), prepared as in step 8, in dry CH$_2$Cl$_2$ (11.5 mL) was added dropwise 1M PBr$_3$ in CH$_2$Cl$_2$ (3.6 mL, 3.6 mmol) at 0° C. The reaction was stirred at ambient temperature until TLC indicated complete reaction (~5 hours). The resulting solution was partitioned between ethyl acetate and brine. The combined organic layers were decolorized with charcoal, dried (MgSO$_4$), filtered through celite and concentrated in vacuo. Purification by flash chromatography on silica gel (40% ethyl acetate/hexane) provided 4-(N-acetyl-N-methylamino)benzyl bromide as a colorless solid (595 mg, 81.0%). $^1$H NMR (300 MHz, CDCl$_3$) δ 7.46 (2H, d, J=8.5 Hz), 7.18 (2H, d, J=8.5 Hz), 4.50 (2H, s), 3.27 (3H, s), 1.88 (3H, br s). MS m/e 242 (M+H)$^+$, 259/261 (M+NH$_4$)$^+$.

Analysis calc'd for C$_{10}$H$_{12}$NOBr: C, 49.61; H, 5.00; N, 5.79. Found: C, 49.35; H, 4.97; N, 5.65.

Step 10. Trans-1,4-dimethoxy-4-[3-(4-(N-acetyl-N-methylamino)benzyloxy)-5-fluorophenyl]cyclohexane Trans-1,4-dimethoxy-4-(3-hydroxy-5-fluorophenyl)-cyclohexane (55.0 mg, 0.22 mmol), prepared as in step 6, was dissolved in dry DMF (2.2 mL) and sodium hydride (13.0 mg, 0.32 mmol) was added to the mixture. After gas evolution ceased, 4-(N-acetyl-N-methylamino)benzyl bromide, (48.0 mg, 0.20 mmol) prepared as in step 9, dissolved in dry DMF (1.0 mL) was added. The reaction was stirred for 1 hour at ambient temperature and quenched by adding excess saturated aqueous ammonium chloride. The resulting biphasic mixture was poured into ethyl acetate and the organic phase was washed (1×saturated aqueous ammonium chloride; 2×brine), dried (MgSO$_4$), filtered and concentrated in vacuo to give an oil. Purification by flash chromatography on silica gel (50% ethyl acetate/hexane) provided trans-1,4-dimethoxy-4[(3-(4-(N-acetyl-N-methylamino)benzyloxy)-5-fluorophenyl]cyclohexane as a colorless oil (57.0 mg, 63.0%). $^1$H NMR (300 MHz, CDCl$_3$) δ 7.50 (2H, br d, J=8.5 Hz), 7.22 (2H, br d, J=8.5 Hz), 6.85 (1H, br s), 6.77 (1H, br dt, J=9.9 1.5, 1.5 Hz), 6.59 (1H, dt, J=9.9, 1.5, 1.5 Hz), 5.06 (2H, s), 3.49 (1H, br s), 3.32 (3H, s), 3.27 (3H, br s), 2.98 (3H, s), 2.03 to 1.90 (4H, m), 1.88 (3H, br s), 1.85 to 1.71 (4H, m). MS m/e 416 (M+H)$^+$, 433 (M+NH$_4$)$^+$.

Analysis calc'd for C$_{24}$H$_{30}$FNO$_4$: C, 69.38; H, 7.28; N, 3.37. Found: C, 69.17; H, 7.44; N, 3.21.

EXAMPLE 2

Preparation of trans-1,4-dimethoxy-4-[3-(4-(N-acetyl-N-methylamino)-benzyloxy)phenyl]cyclohexane The desired compound is prepared according to the method of Example 1, except substituting 3-(napth-2-ylmethyloxy)bromobenzene for 3-(napth-2-ylmethyloxy)-5-fluorobromobenzene.

EXAMPLE 3

Preparation of trans-1,4-dimethoxy-4-[3-(4-(N',N'-dimethylaminocarbonyl-N-methylamino)benzyloxy)-5-fluoro-phenyl]cyclohexane Step 1. Methyl 4-(N-methylaminocarbonyl)aminobenzoate A solution of methyl 4-aminobenzoate (15 g, 99 mmol), and methyl isocyanate (11.8 mL, 200 mmol) in toluene (400 mL) was heated at 100° C. under N$_2$ for 3 hours during which time a precipitate formed slowly. Additional methyl isocyanate (11.8 mL, 200 mmol) was added and heating was continued for 2 hours. The reaction mixture was cooled to 0° C. and filtered. The precipitate was washed with ether and vacuum-dried to give methyl 4-(N-methylaminocarbonyl)aminobenzoate as a colorless solid (17.5 g, 85%).

Step 2. Methyl 4-(N',N'-dimethylaminocarbonyl-N-methylamino)benzoate

To a 0° C. suspension of NaH (80% oil dispersion, 3.60 g, 120 mmol) in THF (200 mL) under N$_2$ was added a solution of methyl 4-(N-methylaminocarbonyl)aminobenzoate (10.0 g, 48 mmol), prepared as in step 1, in THF (40 mL). The reaction mixture was stirred at 0° C. until gas evolution ceased, then the cold bath was removed and stirring was continued for 1.5 hours. A solution of iodomethane (6.6 mL, 106 mmol) in DMF (24 mL) was added and the reaction mixture was stirred for 72 hours at ambient temperature. NaH (2.0 g), and iodomethane (5.0 mL) were then added and the reaction mixture was stirred for an additional 2 hours. The reaction mixture was poured slowly into ice-water and the organics were stripped off in vacuo. The aqueous solution was extracted with ethyl acetate (10×). The combined organic layers were dried over MgSO$_4$, filtered, and concentrated. Pure methyl 4-(N',N'-dimethylaminocarbonyl-N-methylamino)benzoate (6.62 g, 58%) was obtained as a colorless oil which crystallized on standing after chromatography on silica gel (40%, then 50% ethyl acetate/hexanes). mp 71°–73° C.

Step 3. 4-(N',N'-dimethylaminocarbonyl-N-methylamino)benzyl alcohol

To a 0° C. solution of methyl 4-(N',N'-dimethylaminocarbonyl-N-methylamino)benzoate (1.50 g, 6.35 mmol), prepared as in step 2, in THF (11.4 mL) was added lithium triethylborohydride (1.0 M solution in THF, 14 mmol). The reaction mixture was stirred for 1 hour. Water (3.0 mL) and H$_2$O$_2$ (30% aqueous solution, 5.0 mL) were added cautiously and the reaction mixture was stirred at 45° C. for 20 min. Aqueous HCL (6 M, 8.0 mL) was added and the reaction mixture was stirred at reflux for 14 hours. The reaction mixture was cooled to ambient temperature and poured into ethyl acetate. The aqueous phase was extracted three times with ethyl acetate. The combined organic layers were dried over MgSO$_4$, filtered, and concentrated in vacuo. 4-(N',N'-dimethylaminocarbonyl-N-methylamino)benzyl alcohol (797 mg, 61%) was isolated as a colorless solid by chromatography on silica gel (ethyl acetate). mp 65°–66° C.

Step 4. 4-(N',N'-dimethylaminocarbonyl-N-methylamino)benzyl chloride

To a stirred solution at −23° C. under N$_2$ of 4-(N',N'-dimethylaminocarbonyl-N-methylamino)benzyl alcohol (77.0 mg, 0.37 mmol), prepared as in step 4, in dry CH$_2$Cl$_2$ (3.7 mL) was added triethylamine (67.0 µL, 0.48 mmol), and methanesulfonyl chloride (34.0 μL, 0.44 mmol). The reaction mixture was stirred at ambient temperature until TLC indicated complete reaction (~5 hours). The resultant solution was poured into ethyl acetate and the organic phase was washed (2 X, water; 2 X, brine), dried (MgSO4), filtered and concentrated in vacuo. Purification by flash chromatography on silica gel (70% ethyl acetate/hexane) provided 4-(N',N'-dimethylaminocarbonyl-N-methylamino)benzyl chloride (56.0 mg, 67.0%) as a colorless oil which crystallized on standing at −25° C. mp 38.5°-39° C. $^1$H NMR (300 MHz, CDCl3) δ 7.34 (2H, d, J=8.5 Hz), 7.04 (2H, d, J=8.5 Hz), 4.57 (2H, s), 3.22 (3H, s), 2.71 (6H, s). MS m/e 227 (M+H)+, 244 (M+NH4)+.

Step 5. trans-1,4-dimethoxy-4[(3-(4-(N',N'-dimethylaminocarbonyl-N-methylamino)benzyloxy)-5-fluoro-phenyl]cyclohexane The desired compound was prepared according to the method of Example 1, step 10, except substituting 4-(N',N'-dimethylaminocarbonyl-N-methylamino)benzyl chloride, prepared as in step 4, for 4-(N-acetyl-N-methylamino)benzyl bromide. $^1$H NMR (300 MHz, CDCl3) δ 7.48 (2H, d, J=8.5 Hz), 7.07 (2H, d, J=8.5 Hz), 6.82 (1H, br t, J=1 Hz), 6.75 (1H, ddd, J=9.5, 2, 1.5 Hz), 6.58 (1H, dt, J=9.5, 2.0, 2.0 Hz), 4.99 (2H, s), 3.49 (1H, br s), 3.32 (3H, s), 3.23 (3H, br s), 2.98 (3H,s), 2.72 (6H, s), 1.72-2.02 (8H, m). MS m/e 445 (M+H)+, 462 (M+NH4/)+.

Analysis calc'd for C25H33FN2O4(0.5 H2O): C, 66.20; H, 7.56; N, 6.18. Found: C, 66.54; H, 7.16, N, 6.07.

EXAMPLE 4

Preparation of trans-1,4-dimethoxy-4-[3-(4-(N',N'-dimethylaminocarbonyl-N-methylamino)benzyloxy)phenyl]cyclohexane The desired compound is prepared according to the method of Example 3, except substituting trans-1,4-dimethoxy-4-(3-hydroxyphenyl)cyclohexane, prepared as in Example 2, for trans-1,4-dimethoxy-4-(3-hydroxy-5-fluorophenyl)cyclohexane.

EXAMPLE 5

Preparation of trans-1,4-dimethoxy-4-[3-(4-(N',N'-dimethylaminocarbonyl-N-methylamino) phenylthio)phenyl]cyclohexane Step 1. Preparation of N-t-Boc-4-iodoaniline The desired compound was prepared by heating a solution of 4-iodoaniline and di-tert-butyldicarbonate in 2M aqueous sodium hydroxide at reflux, followed by cooling to ambient temperature and extraction of N-t-Boc-4-iodoaniline with ethyl acetate. mp 140°-141° C. $^1$H NMR (300 MHz, CDCl3) δ 7.57 (2H, d, J=9 Hz), 7.13 (2H, d, J=9 Hz), 6.43 (1H, br s), 1.52 (1H, br s). MS m/e 320 (M+H)+, 337 (M+NH4)+.

Step 2. Preparation of 3-(4-aminophenylthio)bromobenzene

A mixture of 3-bromothiophenol (3.00 g, 15.9 mmol), N-t-Boc-4-iodoaniline (5.00 g, 15.9 mmol), prepared as in step 1, CuI (756 mg, 4.00 mmol), and K2CO3 (4.40 g, 31.7 mmol) in DMF was heated at reflux under N2 for 2 hours. The reaction mixture was poured into H2O/ethyl acetate and filtered through a pad of celite. The organic phase was washed twice with saturated aqueous NH4Cl, once with H2O, and twice with brine, dried over MgSO4, filtered, and concentrated in vacuo. Chromatography on silica gel (20% ethyl acetate/hexanes) provided 3-(4-aminophenylthio)bromobenzene (1.56 g, 35%). $^1$H NMR (300 MHz, CDCl3) δ 7.32 (2H, dt, J=9, 2, 2 Hz), 7.18-7.24 (2H, m), 6.97-7.07 (2H, m), 6.69 (2H, dt, J=9, 2, 2 Hz), 3.85 (2H, br s). MS m/e 280/282 (M+H)+, 297/299 (M+NH4)+.

Step 3. Preparation of 3-[4-(N',N'-dimethylaminocarbonylamino)phenylthio]bromobenzene To a solution of 3-(4-aminophenylthio)bromobenzene (415 mg, 1.48 mmol), prepared as in step 2, in CH2Cl2 (7.4 mL) was added triethylamine (0.31 mL, 2.22 mmol) and dimethylcarbamyl chloride (0.34 mL, 3.70 mmol). The reaction mixture was stirred for one hour at ambient temperature and then at reflux for 18 hours, at which time additional triethylamine (3.0 mL), and dimethylcarbamyl chloride (3.0 mL) were added. The reaction mixture was heated at reflux for one hour, then cooled to ambient temperature and poured into ethyl acetate. The solution was washed twice with H2O, twice with brine, dried over MgSO4, filtered, and concentrated in vacuo. Chromatography on silica gel (40% ethyl acetate/hexanes) provided 3-[4-((N',N'-dimethylaminocarbonyl)amino)phenylthio ]bromobenzene (362 mg, 70%) as a colorless oil. $^1$H NMR (300 MHz, CDCl3) δ 7.37-7.45 (4H, m), 7.23-7.28 (2H, m), 7.06-7.10 (2H, m), 6.38 (1H, br s), 3.07 (6H, s). MS m/e 353/353 (M+H)+, 368/370 (M+NH4)+.

Step 4. Preparation of 3-[4-(N',N'-dimethylaminocarbonyl-N-methylamino)phenylthio]bromobenzene To a solution of 3-[4-(N',N'-dimethylaminocarbonylamino)phenylthio]bromobenzene (100 mg, 0.285 mmol), prepared as in step 3, in DMF (2.8 mL) was added NaH (60% oil dispersion, 30.0 mg, 0.745 mmol). The reaction mixture was stirred at ambient temperature for one hour. Iodomethane (22.3 μL, 0.358 mmol) was added and the reaction mixture was stirred at ambient temperature for 17 hours. The reaction mixture was quenched with saturated aqueous NH4Cl and poured into ethyl acetate. The organic phase was washed once with saturated aqueous NH4Cl, once with H2O, and twice with brine, dried over MgSO4, filtered, and concentrated in vacuo. 3-[4-(N',N'-dimethylaminocarbonyl-N-methylamino)phenylthio]bromobenzene (89.2 mg, 86% ) was obtained by chromatography on silica gel (40% ethyl acetate/hexanes). $^1$H NMR (300 MHz, CDCl3) δ 7.38 (2H, dt, J=9, 2, 2 Hz), 7.29-7.33 (2H, m), 7.13-7.16 (2H, m), 7.03 (2H, dt, J=9, 2, 2 Hz), 3.24 (3H, s), 2.75 (6H, s). MS m/e 365/367 (M+H)+, 382/384 (M+NH4)+.

Step 5. Trans-1,4-dimethoxy-4-[3-(4-(N',N'-dimethylaminocarbonyl-N-methylamino)phenylthio)-phenyl]cyclohexane The desired compound is prepared according to the method of Example 1, steps 1-5, except substituting 3-[4-(N',N'-dimethylaminocarbonyl-N-methylamino)-phenylthio]bromobenzene, prepared as in step 4, for 3-(napth-2-ylmethyloxy)-5-fluorobromobenzene.

EXAMPLE 6

Preparation of trans-1,4-dimethoxy-4-[3-(4-(N',N'-dimethylaminocarbonyl-N-methylamino)phenylsulfinyl) phenyl]cyclohexane.

The desired compound is prepared by treatment of trans-1,4-dimethoxy-4[3(4-(N',N'-dimethylaminocarbonyl-N-methylamino)phenylthio)phenyl]cyclohexane, prepared as in Example 5, with sodium metaperiodate as described in EPA 409 413.

EXAMPLE 7

Preparation of
trans-1,4-dimethoxy-4-[3-(4-(N'N'-dimethylaminocarbonyl-N-methylamino)phenylsulfonyl)
phenyl]cyclohexane The desired compound is prepared by treatment of trans-1,4-dimethoxy-4[3(4-(N',N'-dimethylaminocarbonyl-N-methylamino)phenylthio)phenyl]cyclohexane, prepared as in Example 5, with potassium peroxymonosulphate as described in EPA 409 413.

EXAMPLE 8

Preparation of
trans-1,4-dimethoxy-4-[(3-(4-(N',N'-dimethylaminothiocarbonyl-N-methylamino)benzyloxy)-5-fluorophenyl]cyclohexane The desired compound is prepared by treatment of trans-1,4-dimethoxy-4[(3-(4-(N',N'-dimethylaminocarbonyl-N-methylamino)benzyloxy)-5-fluorophenyl]cyclohexane, prepared as in Example 3 with Lawesson's Reagent ([2,4-bis(4-methoxyphenyl)-1,3-dithia-2,4-diphosphetane-2,4-disulfide) according to the method of Katah, A., Kashima, C., and Omote, Y. *Heterocycles*, 1982, 19(12), 2283.

EXAMPLE 9

Preparation of
trans-1,4-dimethoxy-4-[3-(4-(N-acetyl-N-methylamino)-phenylthio)phenyl]cyclohexane Step 1. 3-(4-(N-acetylamino)phenythio)bromobenzene The desired compound is prepared according to the method of Example 1, step 7, except substituting 3-(4-aminophenylthio)bromobenzene, prepared as in Example 5, step 2, for N-methyl-4-aminobenzoic acid.

Step 2. 3-(4-(N-acetyl-N-methylamino)phenylthio)-bromobenzene

The desired compound is prepared according to the method of Example 5, step 4, except substituting 3-(4-(N-acetyl-N-methylamino)phenylthio)bromobenzene, prepared as in step 1, for 3-[4-((N',N'-dimethylaminocarbonyl)amino)phenylthio]bromobenzene.

Step 3. Trans-1,4-dimethoxy-4-[3-(4-(N-acetyl-N-methylamino) phenylthio)phenyl]cyclohexane The desired compound is prepared according to the method of Example 1, steps 1–5, except substituting 3-[4-(N-acetyl-N-methylamino)phenylthio]bromobenzene, prepared as in step 2, for 3-(napth-2-ylmethyloxy)-5-fluorobromobenzene.

EXAMPLE 10

Preparation of
trans-1,4-dimethoxy-4-[3-(4-(N-acetyl-N-methylamino) phenylsulfinyl)phenyl]cyclohexane The desired compound is prepared according to the method of Example 6, except substituting trans-1,4-dimethoxy-4-[3-(4-(N-acetyl-N-methylamino)phenylthio)phenyl ]cyclohexane for trans-1,4-dimethoxy-4[(3-(4-(N', N'-dimethylaminocarbonyl-N-methylamino)-phenylthio)phenyl]cyclohexane.

EXAMPLE 11

Preparation of
trans-1,4-dimethoxy-4-[3-(4-(N-acetyl-N-methylamino) phenylsulfonyl)phenyl]cyclohexane The desired compound is prepared according to the method of Example 7, except substituting trans-1,4-dimethoxy-4-[3-(4-(N-acetyl-N-methylamino)phenylthio)phenyl]cyclohexane for trans-1,4-dimethoxy-4-[3-(4-(N', N'-dimethylaminocarbonyl-N-methylamino)-phenylthio)phenyl]cyclohexane.

EXAMPLE 12

Preparation of
trans-1,4-dimethoxy-4-[3-(4-(N',N'-dimethylaminocarbonyl-N-methylamino)'
benzylthio)-5-fluorophenyl]cyclohexane Step 1. 3-benzylthio-5-fluorobromobenzene The desired compound is prepared by reaction of benzyl mercaptan with NaH and 1-bromo-3,5-difluorobenzene in THF.

Step 2. Trans-1,4-dimethoxy-4-(3-benzylthio-5-fluorophen-1-yl)cyclohexane

The desired compound is prepared according to the method of Example 1, steps 1–4, except substituting 3-benzylthio-5-fluorobromobenzene, prepared as in step 1, for 3-(napth-2-ylmethyloxy)-5-fluorobromobenzene.

Step 3. Trans-1,4-dimethoxy-4-(3-thioxy-5-fluorophen-1-yl)cyclohexane

The desired compound is prepared by treatment of trans-1,4-dimethoxy-4-(3-benzylthio-5-fluorophen-1-yl)cyclohexane, prepared as in step 2, with trifluoroacetic acid and phenol.

Step 4. Trans-1,4-dimethoxy-4-[3-(4-(N',N'-dimethylaminocarbonyl-N-methylamino)benzylthio)-5-fluorophenyl]cyclohexane The desired compound is prepared according to the method of Example 3, step 5, except substituting trans-1,4-dimethoxy-4-(3-thioxy-5-fluorophen-1-yl)cyclohexane, prepared as in step 3, for trans-1,4-dimethoxy-4-(3-hydroxy-5-fluorophenyl)cyclohexane.

EXAMPLE 13

Preparation of
trans-1,4-dimethoxy-4-[3-(4-(N-acetyl-N-methylamino)-benzylthio)-5-fluorophenyl]cyclohexane The desired compound is prepared according to the method of Example 12, except substituting 4-(N-acetyl-N-methylamino)benzyl bromide, prepared as in Example 1, step 9, for 4-(N',N'-dimethylaminocarbonyl-N-methylamino)benzyl chloride.

EXAMPLE 14

Preparation of
trans-1,4-dimethoxy-4-[3-(4-(N',N'-dimethylaminocarbonyl-N-methylamino)
benzylamino)phenyl]cyclohexane Step 1. N-t-Boc-3-bromoaniline 3-bromoaniline (10 g, 58.1 mmol) and di-tert-butyldicarbonate (19.0 g, 87.1 mmol) were dissolved in 2M aqueous sodium hydroxide and heated at reflux for 1 hour. After cooling to ambient temperature, the reaction mixture was extracted with ethyl acetate. The organic layer was washed (saturated aqueous ammonium chloride, 1×; water, 1×; and brine, 2×), dried (MgSO$_4$), filtered, concentrated in vacuo, and dried under high vacuum to provide N-t-Boc-3 bromoaniline as a colorless solid (15.8 g, 100%). mp 83° C. $^1$H NMR (300 MHz, CDCl$_3$) δ 7.66 (1H, br m), 7.08–7.23 (3H, m), 6.46 (1H, br s), 1.52 (9H, s). MS m/e 272/274 (M+H)$^+$, 289/291 (M+NH$_4$)$^+$.

Step 2. 4-methoxy-4-(3-tert-butoxycarbonylaminophenyl)cyclohexan-1-one ethylene glycol ketal The desired compound is prepared according to the method of Example 1, steps 1 and 2, except substituting N-t-Boc-3 bromoaniline, prepared as in step 1, for 3-(naphth-2-ylmethyloxy)-5-fluorobromobenzene.

Step 3. 4-methoxy-4-(3-tert-butoxycarbonylaminophenyl)cyclohexan-1-one.

The desired compound is prepared according to the method of Example 1, step 3, except substituting 4-methoxy-4-(3-tert-butoxycarbonylaminophenyl)cyclohexan-1-one ethylene glycol ketal, prepared as in step 2, for 4-methoxy-4-[3-(naphth-2-ylmethyloxy)-5fluorophenyl]cyclohexan-1-one ethylene glycol ketal. If necessary, the tert-butoxycarbonyl protecting group may be re-introduced as described in step 1.

Step 4. trans-1,4-dimethoxy-4-(3-tert-butoxycarbonylaminophenyl)cyclohexane.

The desired compound is prepared according to the method of Example 1, steps 4 and 5, except substituting 4-methoxy-4-(3-tert-butoxycarbonylaminophenyl)cyclohexan-1-one, prepared as in step 3, for 4-methoxy-4-[3-(naphthylmethyloxy )-5-fluorophenyl]cyclohexan-1-one.

Step 5. trans-1,4-dimethoxy-4-(3-aminophenyl)cyclohexane

The desired compound is prepared by treatment of trans-1,4-dimethoxy-4-(3-tert-butoxycarbonylaminophenyl)cyclohexane, prepared as in step 4, with trifluoroacetic acid.

Step 6. trans-1,4-dimethoxy-4-[3-(4-(N', N'-dimethylaminocarbonyl-N-methylamino)benzylamino) phenyl]cyclohexane The desired compound is prepared according to the method of Example 3, step 5, except substituting trans-1,4-dimethoxy-4-(3-aminophenyl)cyclohexane, prepared as in step 6, for trans-1,4-dimethoxy-4-(3-hydroxy-5-fluorophenyl)cyclohexane.

EXAMPLE 15

Preparation of trans-1,4-dimethoxy-4-[3-(4-(N-acetyl-N-methylamino)-benzylamino)5-fluorophenyl]cyclohexane The desired compound is prepared according to the method of Example 14, except substituting 4-(N-acetyl-N-methyl-amino)benzyl bromide, prepared as in Example 1, step 9, for 4-(N',N'-dimethylaminocarbonyl-N-methylamino)benzyl chloride.

EXAMPLE 16

Preparation of trans-1,4-dimethoxy-4-[3-(3-(4-(N',N'-dimethylaminocarbonyl-N-methylamino) phenyl)trans-prop-1-enoxy)-5-fluorophenyl]tetrahydropyran Step 1. 4-(N',N'-dimethylaminocarbonylamino)iodobenzene A mixture of 4-iodoaniline (4.22 g, 19.3 mmol), triethylamine (2.78 mL), and dimethylcarbamoyl chloride (1.86 mL) in CH$_2$Cl$_2$ (100 mL) was stirred for 1 hour at ambient temperature and 2 hours at 80° C., during which time the CH$_2$Cl$_2$ evaporated. The residue was left standing at ambient temperature for 36 hours and was then partitioned between ethyl acetate (200 mL) and H$_2$O (100 mL). The layers were separated and the organic phase was dried over MgSO$_4$, filtered, and concentrated in vacuo to give a solid. The crude solid was washed with 1:1 ethyl acetate/pentane to give 4-(N',N'-dimethylaminocarbonylamino)iodobenzene (3.2 g, 55% yield). $^1$H NMR (300 MHz, DMSO-d6) δ 8.36 (1H, s), 7.54 (2H, dt, J=9.0, 1.5 Hz), 7.35 (2H, dt, J=9.0, 1.5 Hz), 2.91 (6H, s). MS m/e 291 (M+H)$^+$, 308 (M+NH$_4$)$^+$.

Step 2. 4-(N',N'-dimethylaminocarbonyl-N-methylamino)iodobenzene

The desired compound is prepared according to the method of Example 3, step 2, except substititing, 4-(N',N'-dimethylaminocarbonylamino)iodobenzene, prepared as in step 1, for 4-(N-methylaminocarbonyl-)aminobenzoate. $^1$H NMR (300 MHz, DMSO-d6) δ 7.64 (2H, dt, J=9.0, 1.5 Hz), 7.86 (2H, dt, J=9.0, 1.5 Hz), 3.5 (3H, s), 2.65 (3H, s). MS m/e 305 (M+H)$^+$, 322 (M+NH$_4$)$^+$.

Step 3. 3-[4-(N',N'-dimethylaminocarbonyl-N-methylamino)phenyl]prop-1-ynol

A mixture of 4-(N',N'-dimethylaminocarbonyl-N-methylamino)iodobenzene (3.0 g, 9.9 mmol), propargyl alcohol (0.56 g, 10.0 mmol), CuI (0.82 g, 10.0 mmol), bis(triphenylphosphine)palladium(II)dichloride 0.18 g, 10.0 mmol) and triethylamine (30 mL), was stirred for 18 hours at ambient temperature. Saturated aqueous NH$_4$Cl solution (50 mL) and NH$_4$OH (10 mL) were then added and the reaction mixture was extracted with ethyl acetate. The organic phase was dried over Na$_2$SO$_4$, filtered, and concentrated in vacuo to give 3-[4-(N',N'-dimethylaminocarbonyl-N-methylamino)-phenyl]prop-1-ynol which was used without further purification. $^1$H NMR (300 MHz, DMSO-d6) δ 7.37 (2H, dt, J=9.0, 1.5 Hz), 7.00 (2H, dt, J=9.0, 1.5 Hz), 5.28 (1H, t, J=6.0 Hz), 4.28 (2H, d, J=6.0 Hz). MS m/e 233 (M+H)$^+$, 250 (M+NH4)$^+$.

Step 4. trans-3-[4-(N',N'-dimethylaminocarbonyl-N-methylamino)phenyl]prop-1-enol To a solution of 3-[4-(N',N'-dimethylaminocarbonyl-N-methylamino)phenyl]prop-1-ynol (0.35 g, 1.5 mmol), prepared in step 3 above, in THF (10 mL) at −78° C. was added Red-Al (sodium bis(2-methoxyethoxy)aluminum hydride, 3.4 M in toluene, 0.44 mL, 1.5 mmol). The reaction mixture was stirred for 2 hours at −78° C., 2 hours at ambient temperature, and was then left standing at −20° C. for 18 hours. To the cold reaction mixture was added H$_2$O (5 mL) and a few drops of dilute aqueous HCl. The reaction mixture was warmed to ambient temperature and extracted with ethyl acetate (2×50 mL). The organic phase was dried over MgSO$_4$, filtered, and concentrated in vacuo to give trans-3-[4-(N',N'-dimethylaminocarbonyl-N-methylamino)-phenyl]propen-1-ol (300 mg) which was used without further purification.

Step 5. Trans-1,4-dimethoxy-4-[3-(3-(4-(N',N'-dimethylaminocarbonyl-N-methylamino) phenyl)trans-prop-1-enoxy)-5-fluorophenyl]tetrahydropyran The desired compound is prepared by adding trans-1,4-dimethoxy-4-(3-hydroxy-5-fluorophenyl)cyclohexane, prepared as in Example 1, step 6, to a solution in THF of diethylazodicarboxylate and triphenylphosphine, followed by addition of trans-3-[4-(N',N'-dimethylaminocarbonyl-N-methylamino)phenyl]propen-1-ol, which is prepared as in step 4 above.

EXAMPLE 17

Preparation of trans-1,4-dimethoxy-4-[3-(3-(4-(N',N'-dimethylaminocarbonyl-N-methylamino)phenyl)prop-1-ynoxy)-5-fluorophenyl]tetrahydropyran The desired compound is prepared according to the method of Example 16, step 5, except substituting 3-[4-(N',N'-dimethylaminocarbonyl-N-methylamino)-phenyl]propyn-1-ol, prepared as in Example 16, step 3, for trans-3-[4(N', N'-dimethylaminocarbonyl-N-methylamino)phenyl]propen-1-ol.

The compounds represented in Table 1 are prepared by acylation of amine 16 with $R^8R^9NCOCl$ as described in Scheme 3.

TABLE 1
Novel N-alkylurea inhibitors of 5-lipoxygenase

| Example | $R^7$ | $R^8$ | $R^9$ |
|---|---|---|---|
| 18 | Me | H | H |
| 19 | Me | H | Me |
| 20 | Me | H | Et |
| 21 | Me | H | Pr |
| 22 | Me | H | Bu |
| 23 | Me | Et | Me |
| 24 | Me | Pr | Me |
| 25 | Me | Bu | Me |
| 26 | Me | Et | Et |
| 27 | Me | Pr | Pr |
| 28 | Me | Bu | Bu |
| 29 | Me | Ph | H |
| 30 | Me | Ph | Me |
| 31 | Me | piperidinyl | |
| 32 | Me | morpholinyl | |
| 33 | Me | thiomorpholinyl | |
| 34 | Me | 4-methylpiperazinyl (H₃C-N) | |
| 35 | Me | piperazinyl (HN) | |
| 36 | Et | H | Me |
| 37 | Et | Me | Me |
| 38 | Pr | H | Me |
| 39 | Pr | Me | Me |
| 40 | Bu | H | Me |
| 41 | Bu | Me | Me |

The compounds represented in Table 2 are prepared as described in Schemes 4 and 5.

TABLE 2
Novel haloalkyl-, hydroxyalkyl-, aminoalkyl-, (alkoxycarbonyl)alkyl-, carboxyalkyl-, and (aminoalkylcarbonyl)alkylurea derivatives of 5-Lipoxygenase.

| Example | $R^7$ | $R^9$ | $R^8$ |
|---|---|---|---|
| 42 | Me | Br-(CH₂)₄- | H |
| 43 | Me | Br-(CH₂)₄- | Me |
| 44 | Me | H₂N-(CH₂)₄- | H |

TABLE 2-continued

Novel haloalkyl-, hydroxyalkyl-, aminoalkyl-, (alkoxycarbonyl)alkyl-, carboxyalkyl-, and (aminoalkylcarbonyl)alkylurea derivatives of 5-Lipoxygenase.

![structure]

| Example | R⁷ | R⁹ | R⁸ |
|---|---|---|---|
| 45 | Me | H₂N–(CH₂)₃– | Me |
| 46 | Me | HO–(CH₂)₄– | H |
| 47 | Me | HO–(CH₂)₄– | Me |
| 48 | Me | HOOC–(CH₂)₃– | H |
| 49 | Me | HOOC–(CH₂)₃– | Me |
| 50 | Me | EtOOC–(CH₂)₃– | H |
| 51 | Me | EtOOC–(CH₂)₃– | Me |
| 52 | Me | CH₃NH–CO–(CH₂)₃– | H |
| 53 | Me | CH₃NH–CO–(CH₂)₃– | Me |

The compounds represented in Table 3 are prepared as described in Scheme 6.

TABLE 3

Novel N-acyl inhibitors of 5-Lipoxygenase

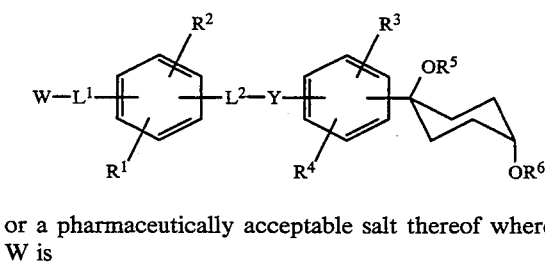

| Example | R⁹ |
|---|---|
| 54 | Br–(CH₂)₃– |
| 55 | NC–(CH₂)₃– |
| 56 | H₂N–(CH₂)₃– |
| 57 | HO–(CH₂)₄– |
| 58 | HOOC–(CH₂)₃– |
| 59 | EtOOC–(CH₂)₃– |
| 60 | CH₃NH–CO–(CH₂)₃– |

We claim:
1. A compound having the structure

$$W-L^1-\text{Ar}(R^1,R^2)-L^2-Y-\text{Ar}(R^3,R^4)-C(OR^5)(\text{cyclohexyl-}OR^6)$$

or a pharmaceutically acceptable salt thereof wherein
W is

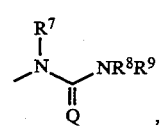         (a)

wherein
  Q is oxygen,
  R⁷, R⁸ and R⁹ are independently selected from the group consisting of hydrogen or alkyl of one to four carbon atoms provided that when L¹ is a bond, R⁷ is alkyl of one to four carbon atoms;
  L¹ and L² are each independently selected from the group consisting of a bond, alkylene of one to three carbon atoms, propenylene, and propynylene;

$R^1$, $R^2$, $R^3$, and $R^4$ are independently selected from the group consisting of
  alkyl of one to four carbon atoms,
  alkoxy of one to four carbon atoms,
  haloalkyl, and
  halogen;
Y is oxygen; and
$R^5$ and $R^6$ are independently selected from the group consisting of
  hydrogen,
  alkyl of one to four carbon atoms,
  alkenyl of two to four carbon atoms, and
  alkynyl of two to four carbon atoms.

2. A compound as defined in claim 1 having the structure

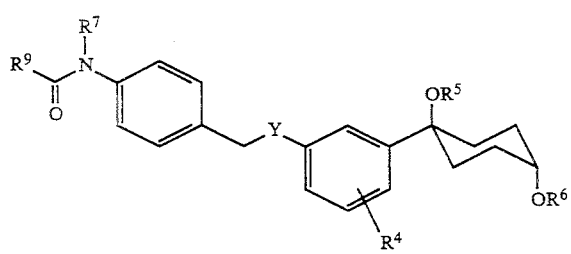

or a pharmaceutically acceptable salt thereof wherein $R^7$ is alkyl of one to four carbon atoms.

3. A compound or pharmaceutically acceptable salt thereof as defined in claim 2 wherein $R^9$ is alkyl of one to four carbon atoms.

4. A compound as defined by claim 1 having the structure

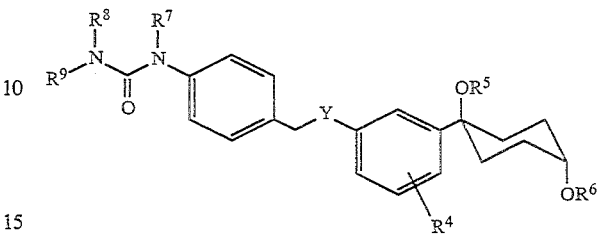

or a pharmaceutically acceptable salt thereof wherein $R^7$ is alkyl of one to four carbon atoms.

5. A compound as defined by claim 4 wherein $R^9$ is alkyl of one to four carbon atoms.

6. A compound or pharmaceutically acceptable salt thereof selected from the group consisting of
  trans-1,4-dimethoxy-4-[3-(4-(N-acetyl-N-methylamino)benzyloxy)-5-fluorophenyl]cyclohexane,
  trans-1,4-dimethoxy-4-[3-(4-(N',N'-dimethylaminocarbonyl-N-methylamino)benzyloxy)-5-fluorophenyl]cyclohexane.

7. A pharmaceutical composition comprising a therapeutically effective amount of a compound as defined by claim 1 in combination with a pharmaceutically acceptable carrier.

* * * * *